United States Patent
Tozzi

(10) Patent No.: US 10,765,440 B2
(45) Date of Patent: Sep. 8, 2020

(54) FOCUSED INTRALUMINAL LITHECTOMY CATHETER DEVICE AND METHODS

(71) Applicant: Sonic Vascular, LLC, Windermere, FL (US)

(72) Inventor: Michael J. Tozzi, Windermere, FL (US)

(73) Assignee: Sonic Vascular, Inc., Windermere, FL (US)

( * ) Notice: Subject to any disclaimer, the term of this patent is extended or adjusted under 35 U.S.C. 154(b) by 116 days.

(21) Appl. No.: 16/188,771

(22) Filed: Nov. 13, 2018

(65) Prior Publication Data

US 2019/0150961 A1    May 23, 2019

Related U.S. Application Data

(60) Provisional application No. 62/585,719, filed on Nov. 14, 2017.

(51) Int. Cl.
*A61B 17/22* (2006.01)
*A61B 17/00* (2006.01)
*A61B 17/225* (2006.01)

(52) U.S. Cl.
CPC .... *A61B 17/22022* (2013.01); *A61B 17/2251* (2013.01); *A61B 2017/00411* (2013.01); *A61B 2017/22008* (2013.01); *A61B 2017/22024* (2013.01); *A61B 2017/22025* (2013.01); *A61B 2017/22062* (2013.01); *A61B 2017/22074* (2013.01)

(58) Field of Classification Search
CPC .............. A61B 17/22; A61B 17/22022; A61B 2017/00411; A61B 2017/22008; A61B 2017/22024; A61B 2017/22025; A61B 2017/22062; A61B 2017/22074
See application file for complete search history.

(56) References Cited

U.S. PATENT DOCUMENTS 6,210,404 B1   4/2001   Shadduck
6,635,054 B2   10/2003  Fjield et al.
(Continued)

OTHER PUBLICATIONS

International Search Report and Written Opinion issued by USPTO in related application No. PCT/US2018/060874, dated Jan. 24, 2019.

*Primary Examiner* — George J Ulsh
(74) *Attorney, Agent, or Firm* — Barnes & Thornburg LLP; Jeffrey R. Stone

(57) ABSTRACT

A system, device and method for removing occlusive material from a bodily lumen comprising a catheter with a distally mounted and fluid-fillable litho-cushion in operative connection with at least one forward-focusing reflector. The catheter comprises a lumen with an electrode pair housing disposed in watertight engagement with the lumen at or near the distal end of the lumen, the electrode pair housing comprising at least one electrode pair. The at least one electrode pair is in wired communication with a pulse generator, wherein the electrode pair is configured to generate an electrical arc between the electrodes of the electrode pair with subsequent generation of a shock wave. The shock wave is directed distally out of the catheter lumen and focused forward and distally away from the catheter lumen by the at least one reflector toward the targeted occlusive material.

21 Claims, 3 Drawing Sheets

(56) References Cited

U.S. PATENT DOCUMENTS

| | | |
|---|---|---|
| 8,257,378 B1 | 9/2012 | O'Connor |
| 9,730,715 B2 | 8/2017 | Adams |
| 2014/0005706 A1* | 1/2014 | Gelfand ............ A61B 17/2202 606/169 |
| 2014/0243715 A1 | 8/2014 | Cioanta et al. |
| 2014/0350401 A1* | 11/2014 | Sinelnikov ......... A61B 17/2202 600/439 |
| 2015/0238208 A1 | 8/2015 | Adams et al. |
| 2016/0022294 A1 | 1/2016 | Cioanta et al. |
| 2017/0303946 A1 | 10/2017 | Ku et al. |

\* cited by examiner

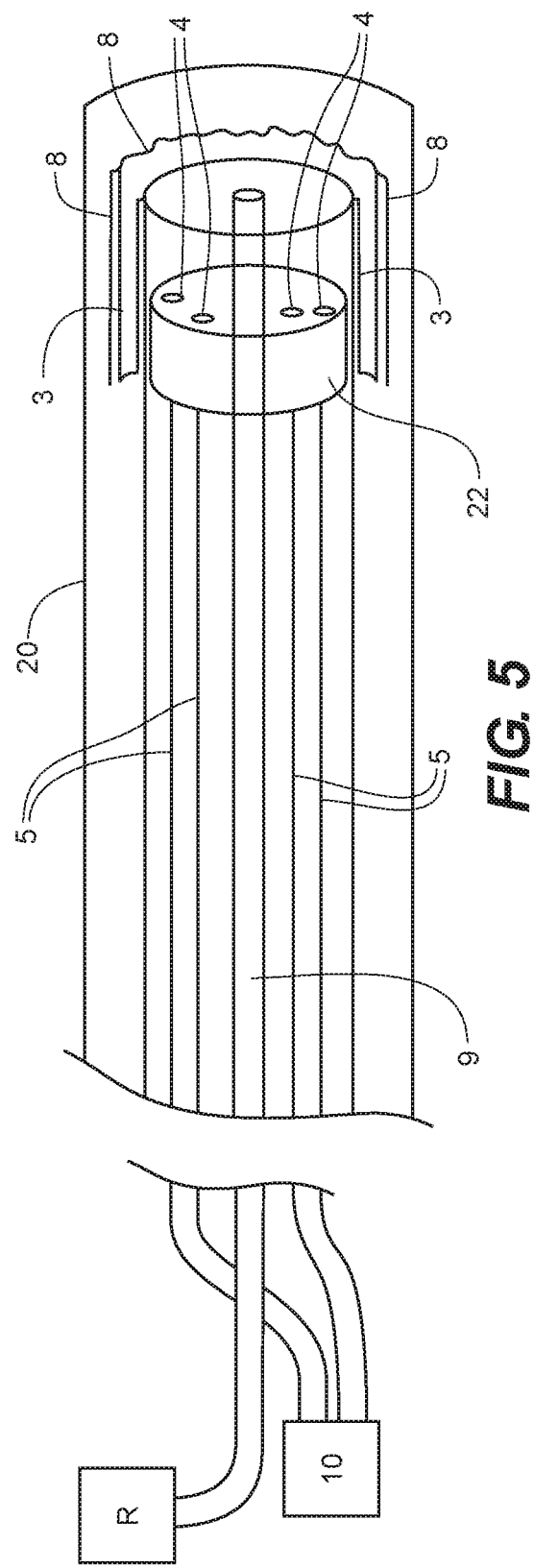

FOCUSED INTRALUMINAL LITHECTOMY CATHETER DEVICE AND METHODS

CROSS-REFERENCE TO RELATED APPLICATIONS

This application claims the benefit of U.S. Provisional Application Ser. No. 62/585,719, filed Nov. 14, 2017 and entitled FOCUSED INTRALUMINAL LITHECTOMY CATHETER DEVICE AND METHODS, THE entirety of which is incorporated herein by reference.

STATEMENT REGARDING FEDERALLY SPONSORED RESEARCH OR DEVELOPMENT

Not Applicable

BACKGROUND OF THE INVENTION

Field of the Invention

The invention relates to a device used to perform intraluminal lithotripsy, more specifically to a lithotripsy catheter for breaking up stenotic material in a blood vessel.

Description of the Related Art

Peripheral artery disease (PAD) refers to diseases of the blood vessels located outside the heart and brain. It is most often caused by a buildup of fatty or calcified deposits in the arteries. PAD affects the blood vessels causing them to narrow, harden and become less flexible therefore restricting the blood flow to the arms, kidneys, stomach, and most commonly, the legs.

An estimated 200 million people worldwide and 12 million people in the U.S. have peripheral artery disease, affecting approximately 12-20 percent of Americans over 60. In the U.S. and Europe, PAD is responsible for around 240,000 amputations every year. Ten percent of these patients die before being discharged from the hospital and almost half within a year of their limb amputation.

Peripheral artery disease is a major risk factor for heart attack and stroke. PAD is more common in African-Americans than other racial groups; and men are slightly more likely than women to develop PAD. Peripheral vascular disease is also more common in smokers.

Symptoms of PAD may include:

Pain, numbness, achiness, or heaviness in the leg muscles. This happens when walking or climbing stairs.

Weak or absent pulses in the legs or feet.

Sores or wounds on the toes, feet, or legs that heal slowly, poorly, or not at all.

A pale or bluish color to the skin.

A lower temperature in one leg than the other leg.

Poor nail growth on the toes and decreased hair growth on the legs.

Erectile dysfunction, especially among men who have diabetes

Treatments for PAD include lifestyle changes, medicines, and surgery or procedures.

Surgical procedures for PAD include:

Bypass Grafting—a surgical procedure to redirect blood flow around an area of blockage, thereby creating an alternate channel for blood flow, bypassing an obstructed or damaged vessel.

Balloon Angioplasty/Stenting—a procedure in which your vascular surgeon inserts a balloon catheter into a narrowed portion of an artery. Expanding the balloon compresses the plaque against the artery wall and reduces the blockage.

Atherectomy—a procedure in which a vascular specialist inserts a specialized catheter into a blocked artery to remove and/or modify a buildup of atherosclerotic plaque from within the vessel.

During such interventions, plaque fracture and dissection of the arterial wall occur frequently especially in the presence of calcium. Balloon angioplasty can cause shear forces that will crack plaque and often separate the plaque from the arterial wall. Although the goal of angioplasty is to increase the lumen, the damage to the artery wall by the balloon can be difficult to control and dissections often occur. This is especially the case when calcium is present. This can result in acute closure of the vessel. There is increasing evidence that medial injury caused during intervention will accelerates the restenosis process thus leading to worsening of symptoms and reinterventions.

Controlling medical injury and dissections during interventions is a common goal for interventionalists. The likelihood of interventional trauma has been related to a number of angiographic features. These characteristics include plaque eccentricity, vessel tortuosity, lesion length and the use of oversized balloons.

The presence of calcium in the vessel creates an elevated risk of injury and dissection. During angioplasty, higher balloon pressures are required to dilate calcified arteries. The presence of calcium requires for a high shear force during balloon inflation and substantially increasing the likelihood of causing damage to the vessel. Although fluoroscopy allows for some visualization of calcium, it does not accurately tell how much calcium is present or the precise location of calcium within the lesion.

In more recent years, interventionalists have turned to atherectomy products for the purpose of debulking, compliance change and/or removing plaque to prepare the vessel for angioplasty and prevent trauma/dissection. These tools have played a key role in the treatment and management of PAD.

As the evolution of atherectomy continues there is a growing demand for discovering a mechanism of action that will most effectively treat/modify harder morphologies such as calcium without causing damage/trauma to healthy tissue. It becomes even more complex when calcified arteries are involved with chronic total occlusions (CTOs).

A catheter that can assist in cannulating CTOs while also treating the most calcified morphologies is in high demand. The use of lithotripsy as the sole mechanism of action for atherectomy with or without the presence of CTO addresses this need. Changing the compliance and/or debulking of calcified arteries so that angioplasty balloons including drug coated balloon can be used thereafter safely and effectively.

The first reports on the fragmentation of human calculi with ultrasound appeared in the 1950s. Initial positive results with an extracorporeal approach with continuous wave ultrasound could, however, not be reproduced. A more promising result was found by generating the acoustic energy either in pulsed or continuous form directly at the stone surface. The method was applied clinically with success.

Extracorporeal shock-wave generators unite the principle of using single ultrasonic pulses with the principle of generating the acoustic energy and focusing it through body walls onto the stone. Häusler and Kiefer reported the first successful contact-free kidney stone destruction by shock wave energy.

The following patents provide a sample of the known art comprising both the extracorporeal and intraluminal application of energy to break up unwanted material in a bodily space or lumen.

U.S. Pat. No. 4,643,186 to Rosen, teaching a catheter with a coaxial transmission line therethrough terminating distally in an antenna capable of creating an electrical arc within a fluid-filled balloon for compression of occluding plaque.

U.S. Pat. No. 8,257,378 to O'Connor, teaching an angioplasty device comprising an energizable ultrasonic transducer inside the distal end of a guide wire, with an inflatable balloon arranged to transmit energy from the transducer through the balloon to the occluding deposits.

U.S. Pat. No. 5,069,664 to Guess, teaching an ultrasonic probe for removal of occlusions.

U.S. Pat. No. 5,524,620 to Rosenschein, teaching a catheter for delivery of high-intensity ultrasound energy to the coronary arteries for removal of thrombosis.

U.S. Pat. No. 6,755,821 to Fry, teaching generation of shockwaves using a lithotripsy probe and balloon system for angiogenesis stimulation in the myocardium.

U.S. Pat. No. 6,527,763 to Esch and U.S. Pat. No. 6,139,543 to Esch, teaching repetitive expansion and collapsing of bubbles to create shockwaves generated by repetitive radiation pulses into a fluid for disruption of occlusions.

U.S. Pat. No. 5,601,738 to Engelhardt, teaching disruption of occlusions using pressure waves from cavitation.

U.S. Pat. No. 6,106,546 to Gregory, teaching pulsing of light energy pulsed to generate pressure waves to treat vasodilation.

U.S. Pat. No. 5,472,406 to de la Torre, teaching a wave generator within a catheter lumen for generating waves to treat vasospasm.

U.S. Pat. No. 6,022,309 to Celliers, teaching catheter-delivered optical energy to generate ultrasonic vibrations for disrupting thrombus.

U.S. Pat. No. 6,428,531 to Visuri, teaching generation of shock waves for occlusion removal using optical fibers.

U.S. Pat. No. 5,709,676 to Alt, teaching the use of optical fibers to generate ultrasonic shock waves in a vessel for impacting plaque.

U.S. Pat. No. 3,942,531 to Hoff, teaching generation of extracorporeal shockwaves for breaking up concrements without physical contact.

U.S. Pat. No. 6,186,963 to Schwarze, teaching the generation of shock waves with at least two electrodes forming a spark discharge gap within a fluid volume with a reflector to concentrate the generated acoustic shock waves.

U.S. Pat. No. 5,152,767 to Sypal, teaching hydraulic shock wave generation using electrodes with focusing reflectors.

U.S. Pat. No. 5,528,578 to Zhong, teaching generation of two shockwave pulses, a first pulse to induce a bubble cluster to form, and a second pulse to force the bubbles to collapse near a target.

U.S. Pat. No. 6,210,404 to Shadduck, teaching a microcatheter adapted for hold two electrodes for producing acoustic waves expelled from the distal end of the catheter.

The company Shockwave Medical, Inc., has a number of patents generally covering the generation of shock waves within a fluid-filled balloon that is pressed against an occlusive material within a blood vessel. At least one mechanical shock wave is formed within the balloon as a result of rapidly expanding and collapsing bubble therein, the energy of which is transmitted through the balloon to the occlusive material. The Shockwave Medical, Inc., solutions require generally a shock wave to move radially/laterally through the fluid-filled balloon to arrive at the occluding material surrounding at least part of the balloon. Consequently, occlusive material located ahead of the device cannot be treated with this device, nor is there a way to focus the generated energy toward the occlusion using reflectors or other technique. Further, also U.S. Pat. No. 9,730,715 (assigned to Shockwave Medical, Inc.) teaches a guidewire with a forward-generated shock wave, wherein the guidewire includes an electrical conductor, wherein the guidewire and conductor are both insulated, with only the electrode(s) exposed. The U.S. Pat. No. 9,730,715 does not require a reflector mechanism, thus the energy generated by the device may not be focused on a specific location.

Accordingly, none of the known art teaches or suggests a lithotripsy system comprising reflectors disposed within the guide or delivery catheter in a first collapsed, and deformed, configuration and that assume an undeformed or biased second expanded configuration when released from the distal end of the catheter. Further, none of the known art teaches the forward-focusing of shockwaves generated by electrodes arcing within a liquid-filled device, wherein the liquid-filled device need not be in contact with the targeted material or occlusion.

Various embodiments of the present invention address these, inter alia, issues.

BRIEF DESCRIPTION OF THE SEVERAL VIEWS OF THE DRAWINGS

FIG. 5 is a cross-sectional view of one embodiment of the present invention.

DETAILED DESCRIPTION OF THE INVENTION

Figure 1:
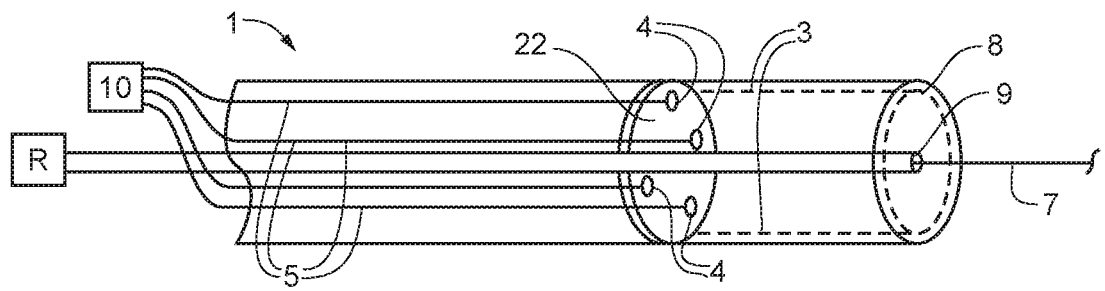
FIG. 1 is a cross-sectional cutaway view of one embodiment of the present invention.
Figure 2:
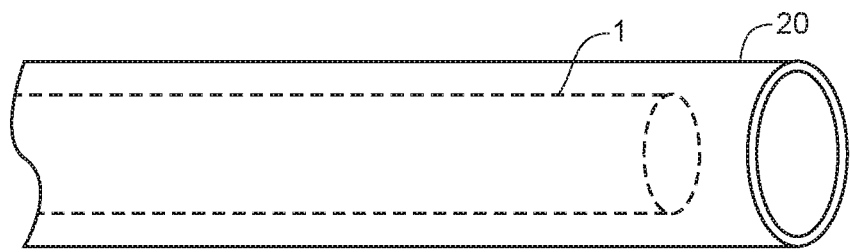
FIG. 2 is a cutaway view of one embodiment of a deployment or guide catheter.

With reference to the Figures, various embodiments of an electric-mechanical generator and catheter for use in lumens or other bodily spaces within the human anatomy. A preferred use for the present invention and methods thereof is found in clearing away stenotic or occlusive material within a blood vessel, e.g., an artery.

This invention is intended, in certain embodiments, for use in creating a lithectomy catheter in the vascular system. More specifically, the removal and/or modification of calcified morphology located within the lesions and/or within the vessel wall associated with vascular disease.

Turning now to the Figures, a high voltage pulse generator (10), located external to the patient's body, and in operative connection and communication with the one or more electrodes (4), provides energy to one or more electrodes (4) that are bonded, or otherwise operatively attached, within and/or to the distal end of a catheter (1). As shown, an electrode pair housing (22) may be provided that may be attached within the lumen L of catheter (1) at or near the distal end of the lumen L.

The electrodes (4) will be connected to a high voltage pulse generator (10) by means of electrical wires (5) that are embedded within the length of the catheter (1), either within the catheter walls and/or running within and along the inner lumen L. These distal electrodes (4) will be housed near the proximal position and proximal boundary of a fluid-fillable litho-cushion (8) and surrounded by reflectors (3) within electrode pair housing (22). Electrode pair housing (22) may comprise a shape that is complementary to the catheter lumen L and, in certain embodiments may be fixed in location at or near the distal end of catheter lumen L. In other embodiments, electrode pair housing (22) may be translatable axially through the lumen L of catheter (1) to enable positioning at or near the distal end of the lumen L of catheter (1) when the catheter is positioned proximate the lesion or occulusion of interest.

The litho-cushion (8) provides for the creation of steam bubbles which in turn will create shockwaves at such time when litho-cushion (8) is filled with fluid and the distal electrode pair (4) is energized with current from the pulse generator (10). The litho-cushion (8) functions to provide a fluid source, e.g., water, for the generation of bubbles and the transmission and/or propagation of energy from shockwaves generated from the expansion and/or collapsing of the generated bubbles.

Litho-cushion (8) comprises a proximal end P that faces and is in fluid communication with the electrode pair(s) (4) and a distal end D that is sealed to retain fluid within the litho-cushion (8) when filled. The electrode pair housing (22) provides fluid sealing on the proximal side of the litho-cushion (8). As shown, a fluid conduit (9) is disposed within the catheter lumen L, with a distal end in fluid communication with the litho-cushion (8) and a proximal end in fluid communication with a fluid reservoir R. Fluid conduit (9) passes through an aperture A in electrode pair housing (22), the aperture A and fluid conduit (9) interaction being sealed to retain fluid within the litho-cushion (8) when filled.

The proximal end P of litho-cushion (8) may be sealingly attached to the distal portion of catheter (1) or to the outer circumference of the electrode pair housing (22). In some embodiments, a distal end of the litho-cushion (8) may be sealed to the fluid conduit (9) which may also serve as a guide wire lumen to allow translation of the guide wire or lithowire (7) therethrough, thus enabling an over-the-wire system as is known in the art.

Litho-cushion (8) may achieve an undeployed configuration for translation through vasculature, wherein the litho-cushion (8) is not filled with fluid. Undeployed litho-cushion (8) may be folded within the catheter lumen L in the case wherein the electrode pair housing (22) is located slightly proximal to the distal end of catheter (1). In some over-the-wire embodiments, the fluid conduit (9) may be pulled proximally to bring the litho-cushion (8) and, in some cases, reflector(s) (3) into the distal end of catheter lumen L in an undeployed configuration.

Alternatively, undeployed litho-cushion (8) may be wrapped tightly around the outer portion of the distal end of catheter (1). Litho-cushion (8) may be urged into a deployed configuration from the undeployed configuration by infusing fluid into the interior of litho-cushion (8) from the reservoir R through the fluid conduit (9). In each case, litho-cushion (8) extends distally from the distal end of the catheter (1) when deployed.

An essential element of various embodiments of the present invention comprises at least one reflector (3) which is located at least partially circumferentially around the proximal lining of the litho-cushion (8). Reflector(s) (3) function to direct shockwaves in a forward (distal) direction so as to maximize energy source toward a forward target such as an occlusion or lesion and may comprise a thin layer of metal such as, without limitation, stainless steel or brass or the like. Other reflective materials are within the scope of the invention and will readily present themselves to the skilled artisan. Alternatively reflector(s) (3) may comprise a discontinuous, and/or perhaps overlapping but disconnected, plurality of reflective elements to provide reflectivity as well as maximizing flexibility to facilitate deployment. The guide wire, or litho-wire (7) will exceed the longitudinal length of the litho-catheter (1) and deployment or guide catheter (20) and may be used to cannulate vascular vessels including chronic total occlusions.

As shown in the Figures, reflectors (3) may in some embodiments be attached to the distal end of the catheter (1) and may comprise a circumferential shape that matches the catheter (1) shape that extends distally past the distal end of catheter (1). Reflector(s) (3) may comprise separate structures that overlap adjacent reflector structures when undeployed and may or may not overlap adjacent reflector structures when deployed. Alternatively, reflector(s) (3) may comprise folded or bunched material when undeployed that expands and/or extends when the reflector(s) (3) are fully deployed. In the latter case, the reflector (3) forms a continuous reflector (3).

In some embodiments, reflectors (3) may be formed with and/or operatively connected to at least a proximal portion of the litho-cushion (8). Thus, reflector(s) (3) may be formed with or connected to the inner side of at least a proximal portion of the litho-cushion (8). Alternatively, reflector(s) (3) may be formed with or connected to the outer side of at least a proximal portion of the litho-cushion (8). In both cases, reflector(s) (3) may be moved from the undeployed configuration to a deployed configuration by inflation of the litho-cushion (8) with fluid. As the litho-cushion (8) expands to deploy, the reflector(s) (3) also expand to deploy. Alternatively or in combination with fluid deployment, reflector(s) (3) may be configured to biasingly expand, by use of biasing springs or equivalent or by virtue of memory shape materials such as nitinol. In the case of a memory shape material, the undeployed reflector (3) will comprise a deformed shape and the deployed reflector (3) comprises an undeformed shape.

Still more alternatively, an outer guide catheter (20) may be provided. In some embodiments, either pushing catheter (1) distally and/or pulling guide catheter (20) proximally so that there is relative translation between the catheter (1) and guide catheter (20) occurs. When the translation proceeds to expose reflector(s) (3), the biasing expansion embodiments will be allowed to expand and deploy. At least partial control of the expansion of the reflector(s) (3) may be achieved by limiting the exposure of the reflector(s) (3) from the guide catheter (20), with full exposure resulting in full deployment.

In other embodiments, reflector(s) (3) may comprise structures that are not connected to the litho-cushion (8), but are in operative contact with the litho-cushion (8) when deployment of the reflector(s) (3) and the litho-cushion (8) is achieved. In these embodiments, litho-cushion (8) is deployed by filling with fluid as described above. Thus, in certain embodiments, the reflector(s) (3) comprise a proximal and a distal end and may be connected at the proximal end with catheter (1), and in other embodiments, the reflector(s) (3) may be connected at the proximal end with the electrode pair housing (22). Reflector(s) (3) deployment may occur by virtue of shape memory material or by biasing spring-like elements as described above with an operative connection with at least the proximal end of litho-cushion (8) upon deployment.

The distal electrode(s) (4) assembly may have a varying depth, dimension or shape. Electrodes of electrode pair(s) (4), which may also be referred to as a lithotripsy emitters (4) will be placed toward the distal end/tip of the litho-catheter (1) but proximal to litho-cushion (8) and connected via electrical wires (5) to a high voltage pulse generator (10). The mechanism of bonding the electrodes of electrode pair(s) (4) to litho-catheter (1) and/or electrode pair housing (22) may be accomplished in any number of ways known in the art. In some variations, there may be multiple electrodes and/or pairs thereof (4) of varying shapes as is well known in the art and that are attached toward the distal end of catheter (1). The electrodes pairs (4) may be housed within the pouch-like and water-tight bag or litho-cushion (8) or, as in preferred embodiments, may be located outside of, or spaced proximally from, the litho-cushion (8), for example within the lumen L of catheter (1) and/or within the space between reflector(s) (3) while still remaining in fluid communication with the fluid within the litho-cushion (8). Thus, in the preferred embodiment, the electrode pairs (4) are located within the catheter lumen L so that when the shockwave is generated it is directed initially forward or distally by the catheter walls. The shockwave then exits the catheter lumen L and encounters the reflector(s) (3) that further direct the shockwave in a forward or distal direction toward the target.

As described above, when un-deployed the litho-cushion (8) may be wrapped tightly around the catheter (1) until ready for use. At such time, the litho-cushion (8) will be inflated by syringe or inflation device with fluid. Other variations may include the use of a deployment catheter or guide catheter (20) used for the purpose of deploying the litho-cushion (8) for use. The litho-cushion (8) will allow for the production of steam bubbles created by the arcing of current between the electrodes of an electrode pair (4) and which will convert to shockwaves upon the creation of the steam bubble and/or collapsing or implosion of the steam bubble when the arcing is terminated.

Shockwaves will act as the mechanism of action for atherectomy and plaque modification and other tissue modification, removal and/or remodeling. In order to direct such energy (shock waves) this invention will also include the existence of reflectors (3) that comprise a shape that directs the shockwave distally away from the electrode pair(s) (4) and distally away from the distal end of catheter (1) toward a target in an exemplary plaque deposit or other material targeted for disruption. These reflectors (3) may be a part of the configuration of the litho-cushion (8) and may be positioned on the proximal end of the litho-cushion (8) facing forward (distal). The reflectors (3) may be positioned perpendicularly and or circumferentially within the proximal inner or outer lining or surface of the litho-cushion (8). When deployed by either inflation and or pulling back outer guide catheter (20), these reflectors (3) may biasingly extend outward and allow for an exemplary lateral cone-like positioning to the electrode pair(s) (4), thus directing the shockwave toward a lesion.

Thus, as shown in the Figures, during translation of the device to the target site within a bodily space, e.g., to an occlusion within a blood vessel, the litho-cushion (8) and reflector(s) (3) are in a first undeployed configuration. The litho-cushion (8) is generally devoid of fluid at this stage of the procedure and, therefore, takes on a flattened form and may be stored within the distal end of the catheter lumen L for translation to the targeted lesion. The distal end(s) of the reflector(s) (3) may be folded inward toward the longitudinal axis of the catheter (1), with a hinge point, or the equivalent, located at the point of attachment.

The reflector(s) (3) may comprise a biased expanded form so that achieving the undeployed configuration involves a deformation of the structure and overcoming a biasing force to enable the reflector(s) (3) to fit within the catheter lumen L as shown in FIG. 1. When reflector(s) (3) are released from the distal end of the catheter lumen L, an at least one second expanded configuration may be achieved as the reflector(s) (3) begin to achieve their undeformed shape. In the embodiment comprising an outer guiding catheter (20), the reflector(s) (3) may be disposed on the outer portion of catheter (1) in an undeployed configuration as they are held in place along the outer wall of catheter (1) by the presence of the inner wall of the outer guiding catheter (20). In this case, either translating the guiding catheter (20) and the catheter (1) relative to each other results in a release of the reflector(s) (3) to biasingly expand to achieve the at least one second expanded configuration.

Thus, as shown in the Figures, during translation of the device to the target site within a bodily space, e.g., to an occlusion within a blood vessel, the litho-cushion (8) moves from a collapsed, empty configuration to an expanded, at least partially fluid-filled configuration, and reflector(s) (3) move from a deformed, collapsed configuration to at least one undeformed, expanded configuration.

Figure 3:
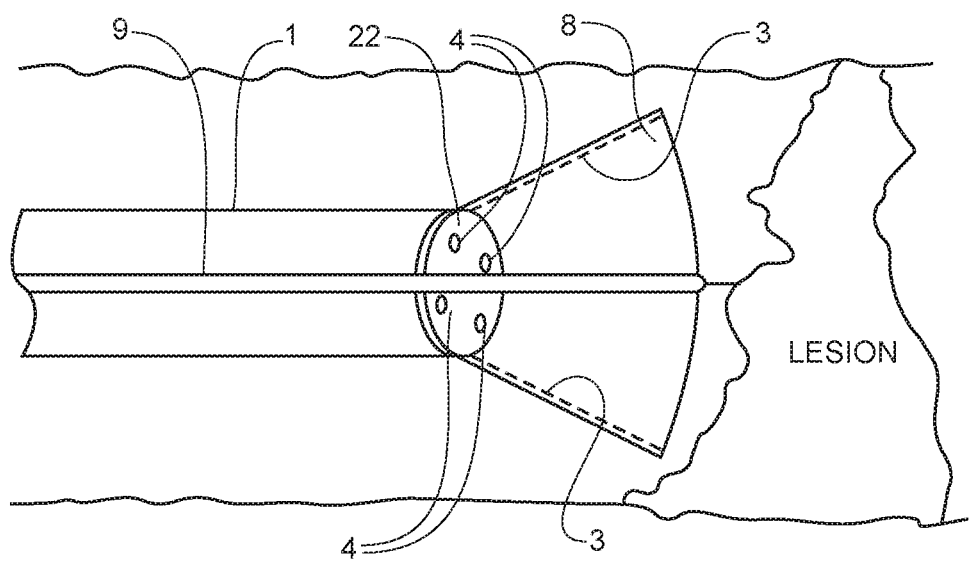
FIG. 3 is a cross-sectional cutaway view of one embodiment of the present invention.

FIG. 1 illustrates the reflector(s) (3) disposed on the outer surface or lining of the litho-cushion (8), while FIG. 3 illustrates the reflector(s) (3) disposed on the inner surface or lining of the litho-cushion (8), each of which as discussed above.

In another embodiment, a high voltage generator (10) provides energy to at least one pair of electrodes (4) that is bonded to the distal end of a catheter (1). The electrodes of the electrode pair(s) (4) are in wired connection with a high voltage pulse generator (10) by means of electrical wires that are embedded within the length of catheter (1). The non-insulated region at the distal ends of the electrodes of electrode pairs (4) are housed within a litho-cushion (8) and surrounded by reflectors (3). The litho-cushion (8) provides for the creation of shockwaves when filled with fluid and the distal electrode pair (4) is energized, creating an arc between the electrodes of electrode pair (4). The litho-cushion's (8) sole purpose is to provide a water or fluid source for the mechanism of action known as lithotripsy. The litho-cushion (8) is not intended or constructed to have or share any of the utilities of a balloon. Reflectors (3) will direct shockwaves in a forward direction so as to maximize energy source toward a target lesion or occlusion or other material located distally from the end of the catheter (1).

As discussed above, the electrodes of the electrode pair(s) (4) may have a varying depth, dimension or shape. The electrode pair(s) (4), also referred to as a shockwave emitter, may preferably be placed flush or co-planar with, or otherwise disposed on, the distal end of a catheter (1). Stated differently, in one embodiment electrode pair(s) (4) may be located on or near the distal-most face of the distal end of catheter (1), and may be incorporated within the wall material of the catheter (1). As above, electrode pair(s) (4) are connected via electrical wires to a high voltage generator (10) located outside of the catheter. The mechanism of bonding the electrodes of the electrode pair(s) (4) to catheter (1) may be accomplished in any number of ways but will preferably be located on the most distal tip of catheter (1). In some variations, there may be a plurality of electrode pair(s) (4) comprising varying shapes that are attached to the distal end or tip of catheter (1). The electrode pair(s) (4) may be housed near the proximal area of the litho-cushion (8) or may be located within the litho-cushion (8).

In this embodiment and when un-deployed, the litho-cushion (8) will be wrapped tightly around the catheter (1), or stored within the distal end of the catheter lumen L, until ready for use at which time it may be deployed in a number of different ways, e.g., by spring, nitinol force, inflated by syringe or by use of outer guide catheter. The fluid-filled litho-cushion (8) allows for the production of bubbles therein and generation of shockwaves as described above that will act as the mechanism of action for lithectomy.

In order to direct such energy (shockwaves) this invention may also include the existence of reflectors (3) as described above in more detail and that may comprise ellipsoidal reflectors but may be shaped in a cone or conical, or may be of any forward-reflecting shape.

These reflectors (3) may be a part of the configuration of the litho-cushion (8) and be positioned near the proximal end of the litho-cushion (8) facing forward (distal). The reflectors (3) and the litho-cushion (8) may be of the same construction or the reflectors may be a connected and remain a part of the catheter (1).

The reflectors (3) may be positioned perpendicularly within the inner lumen L of the catheter (1) or disposed along the outer surface of catheter (1) while in packaged state. When deployed by either inflation, spring or pulling back outer guide catheter, these reflector(s) (3) will extend outward and allow for a lateral cone like positioning to the electrode. Alternatively, reflector(s) (3) may be advanced distally to deploy using a push wire or equivalent.

In all of the embodiments, a fluid reservoir F will be located externally to the patient with a conduit (9) disposed within the inner lumen L of the catheter (1) and extending between the fluid reservoir F and the litho-cushion (8), thereby providing a controlled means for at least partially filling the litho-cushion (8) with the stored fluid.

Figure 4A:
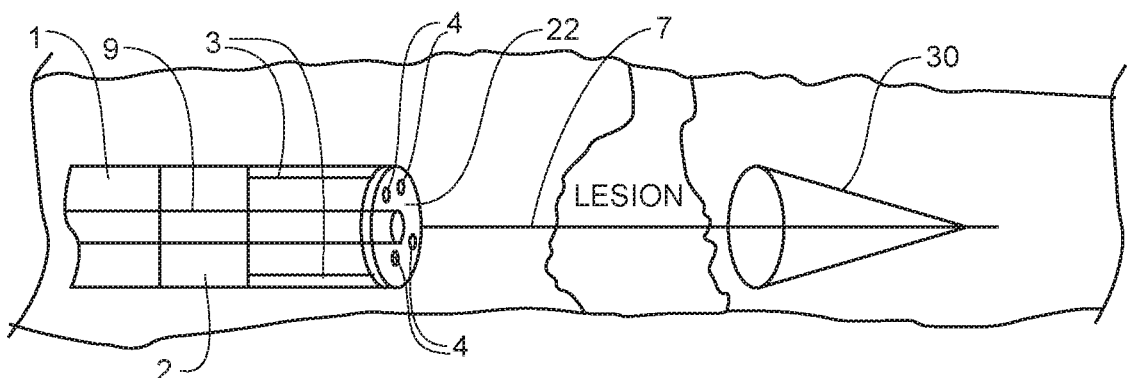
FIGS. 4A-4D provide cross-sectional cutaway views of exemplary steps in a procedure using an embodiment of the present invention.

FIGS. 4A-4D illustrate an exemplary procedure using embodiments of the present invention. Thus, FIG. 4A illustrates catheter (1) with reflectors (3) disposed proximal to electrode pair housing (22) comprising electrode pairs (4). Fluid conduit (9) is disposed within catheter lumen L and a guide wire (7) translated therethrough to an optional distally positioned embolic protection device (30) which, when used, is positioned on a distal side of the occlusive material.

Figure 4B:
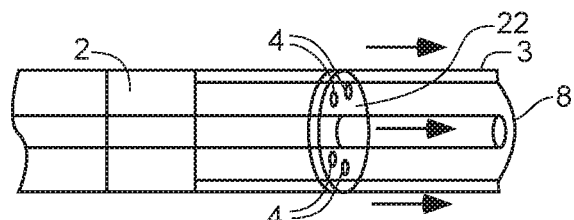
Figure 4C:
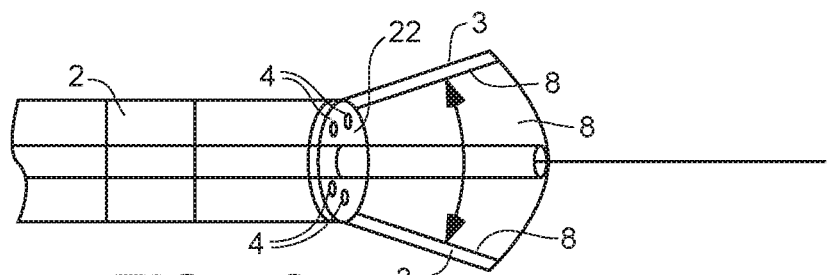
Figure 4D:
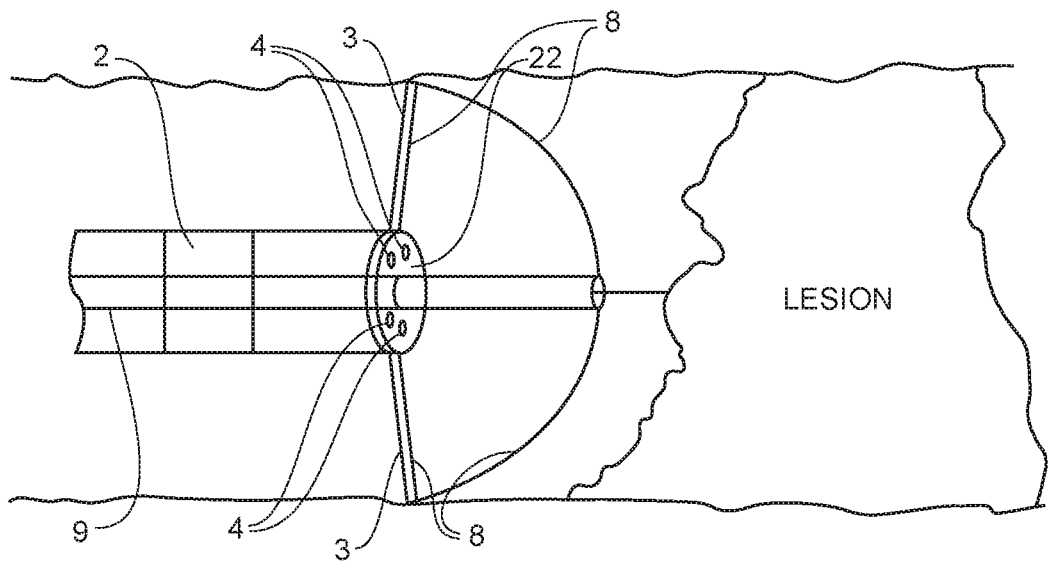

FIG. 4B illustrates the embodiment wherein reflectors (3) are advanced distally to deploy, with deployment of reflectors (3) and inflation of litho-cushion (8) shown in FIG. 4C. Full deployment and inflation is shown in FIG. 4D. Certain embodiments provide a marker such as a fluorescent or radiopaque marker (2) positioned proximal of electrode pair housing (22). Further, an over-the-wire embodiment is shown to allow the guide wire (7) to extend distally through and away from the litho-cushion (8). Once deployed, pulse generator (10) is actuated to send current through the conductive wires connecting the generator (10) with the electrode pairs (4) to generate an arc therebetween and resulting shock wave. The shock wave is transmitted or propagated through the fluid of the litho-cushion (8) and reflected forward by the reflectors (3) toward lesion. In some cases, litho-cushion (8) may be touching the lesion, but this is not required to transmit the shock wave as the vessel comprises fluid which will function to transmit the shock wave energy from the litho-cushion (8) to the lesion.

FIG. 5 illustrates catheter (1) within the lumen of outer guide catheter (20), wherein the reflector(s) (3) are disposed on the inner surface or lining of the litho-cushion (8) in an undeployed configuration.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A system for removing material within a bodily lumen of a patient, comprising:
    a pulse generator configured to be located externally to the patient;
    a catheter comprising an inner lumen with a distal end and at least one pair of electrodes mounted on an electrode pair housing disposed within the inner lumen of the catheter and spaced proximally from the distal end of the inner lumen of the catheter, wherein the electrode pair housing provides a watertight seal within the inner lumen and wherein the at least one pair of electrodes is in operative wired connection with the pulse generator and is configured to generate arcing between the electrodes of the at least one electrode pair when energized by the pulse generator;
    a fluid-fillable and watertight litho-cushion comprising a proximal end sealed to the catheter and in fluid communication with a fluid conduit disposed within the inner lumen of the catheter and a fluid reservoir and in further fluid communication with the portion of the inner lumen of the catheter distal to the electrode pair housing, wherein the litho-cushion is configured to inflate with fluid; and
    at least one forward-focusing reflector adapted to move between an undeployed configuration to a deployed configuration, the at least one forward-focusing reflector extending at least partially distally past the distal end of the inner lumen of the catheter, the at least one forward-focusing reflector in operative connection with the fluid-fillable litho-cushion when deployed and when the litho-cushion is inflated.

2. The system of claim 1, wherein the at least one forward-focusing reflector comprises a biased expanded configuration.

3. The system of claim 2, wherein the at least one forward-focusing reflector comprises a shape memory material.

4. The system of claim 2, wherein the at least one forward-focusing reflector comprises a spring-like element that is biased to expand.

5. The system of claim 1, further comprising an outer guide catheter with a lumen and wherein the catheter is configured to translate within the outer guide catheter lumen.

6. The system of claim 5, wherein the at least one forward-focusing reflector is adapted to deploy when the at least one forward-focusing reflector is translated out of the outer guide catheter lumen.

7. The system of claim 1, wherein the at least one forward-focusing reflector is attached to an outer surface of the catheter and extends distally past the distal end of the catheter lumen.

8. The system of claim 1, wherein the at least one forward-focusing reflector is attached to an inner surface of the catheter and extends distally past the distal end of the catheter lumen.

9. The system of claim 1, wherein the at least one forward-focusing reflector is operatively connected with an outer surface of the litho-cushion.

10. The system of claim 1, wherein the at least one forward-focusing reflector is operatively connected with an inner surface of the litho-cushion.

11. The system of claim 1, wherein the at least one forward-focusing reflector is configured to move from the undeployed configuration to the deployed configuration when the litho-cushion is inflated.

12. The system of claim 9, wherein the at least one forward-focusing reflector is configured to move from the undeployed configuration to the deployed configuration when the litho-cushion is inflated.

13. The system of claim 10, wherein the at least one forward-focusing reflector is configured to move from the undeployed configuration to the deployed configuration when the litho-cushion is inflated.

14. The system of claim 1, wherein the litho-cushion is wrapped around an outer surface of the catheter when not inflated.

15. The system of claim 1, wherein the litho-cushion is disposed within the inner lumen of catheter when not inflated.

16. The system of claim 1, further comprising the fluid conduit extending through the litho-cushion and sealingly attached to a distal portion of the litho-cushion, the fluid conduit comprising a lumen therethrough that is adapted for translation of a guide wire therethrough.

17. The system of claim 1, wherein the at least one forward-focusing reflector is ellipsoidal or conical.

18. The system of claim 1, wherein the electrode pair housing is not translatable within the catheter lumen.

19. The system of claim 1, wherein the electrode pair housing is translatable within the catheter lumen.

20. The system of claim 1, wherein the at least one forward-focusing reflector is configured to be advanced distally to move from the undeployed configuration to the deployed configuration.

21. A method for disrupting occlusive material within a blood vessel, comprising:
    providing the system of claim 1;
    deploying the fluid-fillable litho-cushion by inflating with fluid;
    deploying the at least one-forward-focusing reflector;
    activating the pulse generator and generating an electrical arc between the at least one electrode pair;
    generating a shock wave; and
    focusing the shock wave on the target with the at least one forward-focusing reflector.

* * * * *